(12) United States Patent
Gilman et al.

(10) Patent No.: US 9,168,381 B2
(45) Date of Patent: *Oct. 27, 2015

(54) ARRHYTHMIA ELECTROTHERAPY DEVICE AND METHOD WITH PROVISIONS FOR INFERRING PATIENT DISCOMFORT FROM EVOKED RESPONSE

(71) Applicant: Galvani, Ltd., Edina, MN (US)

(72) Inventors: Byron L. Gilman, Edina, MN (US); Mark W. Kroll, Crystal Bay, MN (US)

(73) Assignee: Galvani, Ltd., Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,273

(22) Filed: Jul. 30, 2014

(65) Prior Publication Data

US 2015/0032170 A1 Jan. 29, 2015

Related U.S. Application Data

(62) Division of application No. 14/103,841, filed on Dec. 11, 2013, now Pat. No. 8,868,178.

(60) Provisional application No. 61/735,832, filed on Dec. 11, 2012.

(51) Int. Cl.
| *A61N 1/37* | (2006.01) |
| *A61N 1/365* | (2006.01) |
| *A61N 1/39* | (2006.01) |
| *A61N 1/362* | (2006.01) |

(52) U.S. Cl.
CPC .............. *A61N 1/3702* (2013.01); *A61N 1/365* (2013.01); *A61N 1/3621* (2013.01); *A61N 1/36542* (2013.01); *A61N 1/3962* (2013.01)

(58) Field of Classification Search
CPC ... A61N 1/3702; A61N 1/3621; A61N 1/365; A61N 1/36542; A61N 1/3962
See application file for complete search history.

(56) References Cited

U.S. PATENT DOCUMENTS

| 4,375,817 A | 3/1983 | Engle et al. |
| 5,782,882 A | 7/1998 | Lerman |
| 5,800,465 A | 9/1998 | Thompson et al. |

(Continued)

FOREIGN PATENT DOCUMENTS

| EP | 0314078 | 10/1988 |
| EP | 0833680 | 3/1997 |

(Continued)

OTHER PUBLICATIONS

Written Opinion and International Search Report for International Application No. PCT/IB2013/002917 dated May 1, 2014.

(Continued)

*Primary Examiner* — Robert N Wieland
(74) *Attorney, Agent, or Firm* — Patterson Thuente Pedersen, P.A.

(57) ABSTRACT

Apparatus and method for treating an arrhythmia in a patient using an electrotherapy device. The device applies a series of electrotherapy pulses in response to the presence of the arrhythmia. In one aspect, indicia of movement by the patient is sensed, and an inference is made whether the movement is an evoked response to the administration of the electrotherapy pulses. Application of subsequent electrotherapy pulses is adjusted in response to an inference of the evoked response constituting discomfort of the patient.

26 Claims, 9 Drawing Sheets

(56) References Cited

U.S. PATENT DOCUMENTS

| | | | |
|---|---|---|---|
| 5,999,852 | A | 12/1999 | Elabbady et al. |
| 6,643,545 | B2 | 11/2003 | Ideker et al. |
| 6,711,422 | B2 | 3/2004 | Mawardi |
| 6,711,442 | B1 | 3/2004 | Swerdlow et al. |
| 6,718,204 | B2 | 4/2004 | Degroot et al. |
| 6,832,982 | B1 | 12/2004 | Lapanashvili et al. |
| 7,164,944 | B1 | 1/2007 | Kroll et al. |
| 7,231,255 | B1 | 6/2007 | Kroll et al. |
| 7,277,755 | B1 | 10/2007 | Falkenberg et al. |
| 7,386,342 | B1 | 6/2008 | Falkenberg et al. |
| 7,509,170 | B2 | 3/2009 | Zhang et al. |
| 7,556,631 | B2 | 7/2009 | Hieshima et al. |
| 7,738,954 | B1 | 6/2010 | Kroll et al. |
| 8,121,680 | B2 | 2/2012 | Falkenberg et al. |
| 8,306,619 | B2 | 11/2012 | Krig et al. |
| 8,423,134 | B2 | 4/2013 | Buschman et al. |
| 8,473,305 | B2 | 6/2013 | Belcher et al. |
| 8,532,793 | B2 | 9/2013 | Morris et al. |
| 8,548,585 | B2 | 10/2013 | Ternes et al. |
| 8,868,178 | B2 | 10/2014 | Gilman et al. |
| 2003/0120316 | A1 | 6/2003 | Spinelli et al. |
| 2004/0210256 | A1 | 10/2004 | Musley et al. |
| 2004/0215258 | A1 | 10/2004 | Lovett et al. |
| 2005/0197676 | A1 | 9/2005 | Kroll et al. |
| 2007/0135847 | A1 | 6/2007 | Kenknight |
| 2008/0039904 | A1* | 2/2008 | Bulkes et al. ............ 607/62 |
| 2008/0234769 | A1 | 9/2008 | Falkenberg et al. |
| 2010/0249860 | A1* | 9/2010 | Shuros et al. ............ 607/4 |
| 2013/0282073 | A1 | 10/2013 | Cowan et al. |
| 2013/0289646 | A1 | 10/2013 | Libbus et al. |

FOREIGN PATENT DOCUMENTS

| | | |
|---|---|---|
| WO | WO 9951300 | 10/1999 |
| WO | WO 2011/163339 | 12/2011 |

OTHER PUBLICATIONS

Joung et al., "Intracellular Calcium and the Mechanism of Anodal Supernormal Excitability in Langendorff Perfused Rabbit Ventricles", National Institutes of Health. Circ J. 2011; 75(4): 834-843.
Application and File History for U.S. Appl. No. 14/103,841, filed Dec. 11, 2013, inventors Gilman et al.

* cited by examiner

Fig. 8B

ARRHYTHMIA ELECTROTHERAPY DEVICE AND METHOD WITH PROVISIONS FOR INFERRING PATIENT DISCOMFORT FROM EVOKED RESPONSE

PRIOR APPLICATIONS

This Application is a division of U.S. patent application Ser. No. 14/103,841, filed Dec. 11, 2013 (Now U.S. Pat. No. 8,868,178), which claims the benefit of U.S. Provisional Application No. 61/735,832 filed Dec. 11, 2012, entitled "Subcutaneous Defibrillator with Methods of Pain Control," the disclosures of each of each being incorporated by reference herein.

FIELD OF THE INVENTION

This disclosure relates generally to the field of electrotherapy apparatus and associated methods and, more particularly, to the treatment of arrhythmias using artificial pacing pulses produced by an implantable subcutaneous device that are capable of causing discomfort in the patient as an undesired side-effect of the treatment.

BACKGROUND OF THE INVENTION

Cardiac arrest is a significant public health problem cutting across age, race, and gender. A positive impact on cardiac arrest survival has been demonstrated with the substantial reduction in time to defibrillation (the administration of a high energy electrical shock to the heart) provided by the widespread deployment of automated external defibrillators and the use of implantable cardioverter defibrillators (ICDs). Defibrillators have had a major impact on dealing with cardiac arrest in that they are the only reliable treatment for ventricular fibrillation (VF.)

Defibrillators can be implanted or external and can include additional capabilities of cardioversion, bradycardia pacing (brady pacing) and anti-tachycardia pacing (anti-tachy pacing or ATP). A recent development in implantable defibrillators is to design the pulse generator and electrodes to be suitable for subcutaneous implantation, thus avoiding the need for an intracardiac electrode. This method has the advantage of potentially simpler surgical procedures and not requiring fluoroscopic facilities to position an intracardiac electrode. Although less invasive than intra-cardiac electrodes, devices utilizing subcutaneous electrodes must apply relatively higher-amplitude pulses to achieve a comparable therapeutic effect as devices employing intra-cardiac electrodes. This requirement is attributable primarily to the greater distance between the subcutaneous electrodes and the resulting wider, less-focused dispersal of charge into the body, making cardiac cell capture less efficient.

In addition to defibrillation, which is often delivered when the patient is unconscious, modern defibrillators also deliver brady pacing, ATP, and cardioversion therapies. In these therapies, the patient is usually conscious and the discomfort associated with subcutaneous delivery of these therapies (particularly ATP and cardioversion) has prevented their use in subcutaneous devices. A solution is needed to mitigate the discomfort associated with these treatments using subcutaneous implantable pulse generators and electrodes.

SUMMARY OF THE INVENTION

One aspect of the present invention is directed to treating an arrhythmia in a patient using an electrotherapy device. The treatable arrhythmia can be a tachycardia or bradycardia. The implantable device can be a subcutaneous pulse generator with subcutaneous electrodes that apply far-field pacing pulses.

In a related aspect of the invention, an electrotherapy device includes a power source adapted to supply energy for operation of the apparatus, electrotherapy administration circuitry electrically coupled to the power source and to a set of patient terminals, and constructed to generate electrotherapy pulses using the energy from the power source and apply a series of the electrotherapy pulses via the patient terminals in response to a control signal, the electrotherapy pulses being far-field pacing pulses, each delivering sufficient charge, through a set of electrodes positioned subcutaneously in far-field fashion relative to a heart of the patient, to initiate a cardiac cycle, and monitoring circuitry electrically coupled with the power source and the set of patient terminals, and constructed to monitor the patient for indicia of the arrhythmia.

Also included is controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses.

The electrotherapy device monitors the patient for indicia of the arrhythmia, determines the presence of the arrhythmia based on the indicia, and applies a series of electrotherapy pulses in response to the presence of the arrhythmia as a result of the determining, each of the pulses of the series having a rising edge, a peak amplitude, and a trailing edge.

In one embodiment, the electrotherapy device applies a first slew rate for a first portion of each rising edge of each pulse of the series of electrotherapy pulses, and a second slew rate for a second portion of each rising edge of each pulse of the series of electrotherapy pulses.

In another embodiment, the electrotherapy administration circuitry includes a pulse shaping circuit constructed such that, in operation, the pulse shaping circuit applies a half-wave sinusoidal pulse wave shape for at least a major part of a duration of each pulse, the sinusoidal pulse wave shape including a rising portion and a falling portion.

In another embodiment, the controller circuitry stores a plurality of approved electrotherapy application vectors, each one of which is associated with a corresponding set of electrotherapy pulse parameters including a minimum peak pulse amplitude limit established during in-situ testing in the patient, and executes a parameter setting input module utilizing communication circuitry to accept configuration instructions to vary the electrotherapy application vector.

In another embodiment, the device includes evoked response sensing circuitry electrically coupled to the controller circuitry, the evoked response sensing circuitry being constructed to sense indicia of movement by the patient, and the controller circuitry being further configured to infer whether the movement is an evoked response to the administration of the electrotherapy pulses, and to adjust application of subsequent electrotherapy pulses in response to an inference of the evoked discomfort response.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

This disclosure addresses methods of reducing the discomfort of ATP and cardioversion and enabling them to be clinically useful in subcutaneous defibrillators as well as traditional ICDs. The basic concepts of ATP and cardioversion are known and have been described in U.S. Pat. Nos. 6,718,204 and 4,375,817, the disclosures of which are incorporated by reference herein, except for any express definitions stated therein insofar as they are inconsistent with the terminology of the present disclosure.

One aspect of the invention is directed to delivering effective electrotherapy for treating cardiac arrhythmias while mitigating the discomfort experienced by the patient as a result of the treatment. Patient discomfort in the present context includes pain or, more generally, an unpleasant sensation, along with the largely psychological discomfort from an involuntary muscle flinch due to motor neuron stimulation as a byproduct of the cardiac stimulation.

One type of application for this aspect of the invention is in far-field anti-tachycardia pacing (ATP) (e.g., as implemented with a subcutaneous implanted device), where the pacing pulse has a large enough amplitude to be felt by the patient. Other applications can include far-field electro-stimulation of the heart where pulse amplitudes are in the range of 30 mA-80 mA.

According to one embodiment, discomfort of the patient is mitigated by applying pacing pulses targeting the heart with a reduced spectral power in the higher frequencies compared with conventional pulses applied by present-day implantable pulse generators. For instance, the pulses according to this embodiment and have slower rise and fall times (i.e., a slower slew rate). This approach recognizes the fact that sharp pain receptors (e.g., thinly myelinated type III (A-delta) fibers) have time constants generally in the range of 100-600 µs, whereas the effective time constant associated with myocardial cells is in the range of 1-5 ms—notably, an order of magnitude slower than the time constant associated with the pain receptors. According to one particular embodiment, the electrotherapy pulses are 3-15 ms in duration. In a related embodiment, the pulses have a duration in the range of 4-8 ms. In a specific case, a particular pulse duration of 5 ms is employed.

For pulse durations in this range, cardiac capture is largely a function of the delivered charge in the pulse. Although the actual charge required for cardiac capture increases with duration, this increases at a much slower rate than it does for nerve stimulation since the cardiac cell chronaxie is greater. Thus, in a related embodiment, the pulse waveform characteristic is such that a sufficient charge is delivered to achieve reliable cardiac capture, while the amplitude profile is such that sharp peaks are avoided. By reducing the peak amplitude relative to conventional waveforms used with subcutaneous treatments, this waveform can reduce the patient's discomfort, and by lengthening the pulse width the equivalent total charge is delivered as with higher-peak waveforms. This approach accepts a modest trade-off in stimulation efficacy and energy efficiency compared with conventional waveforms.

Figure 1:
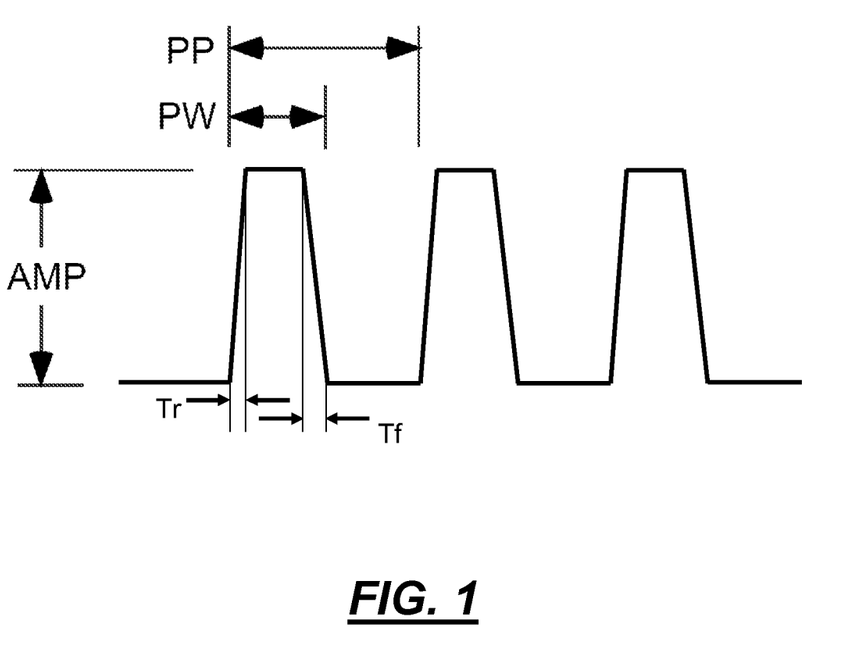
FIG. 1 is a waveform diagram illustrating various conventional pacing parameters, certain values of which can be used to mitigate discomfort associated with electrotherapy according to aspects of the invention.

A generalized depiction of an electrotherapy pacing waveform is shown in FIG. 1. The general waveform is composed of a plurality of pulses that are timed to coincide with the heart rate to be controlled. The pulse period PP is the inverse of this rate. The individual pulses, from start to finish, have a defined pulse width PW. For each pulse, there is a rising edge having a rise time Tr, and a falling, or trailing, edge having a fall time Tf as shown. Each pulse has a peak amplitude labeled AMP.

As an illustrative example, for anti-tachycardia pacing and anti-bradycardia pacing, Table 1 below provides an exemplary range of parameter values corresponding to empirically determined effectiveness.

TABLE 1

Exemplary Parameter Value Ranges for Implanted Pacing Devices

| Parameter | Value of Parameter ATP Device | Value of Parameter Antibradicardia Device |
| --- | --- | --- |
| Pulse Rate | 150-250 per min. | 50-100 per min. |
| Pulse Current Amplitude | 30-80 mA | 15-75 mA |
| Pulse Width | 3-15 ms | 3-15 ms |
| Pulse Period | 240-400 ms | 600-1200 ms |
| Rise time | 0.05-4 ms | 0.05-4 ms |
| Fall time | 0.05-4 ms | 0.05-4 ms |

The wave shape of each pulse is defined by these parameters, along with other parameters that establish the time-varying characteristic of each part of the pulse. For instance, in the simple example depicted in FIG. 1, we have trapezoidal pulse waveforms in which the rising and falling edges are linear, and where the peak amplitude is maintained at a steady level for a significant portion of each pulse's duration.

Figure 2A:
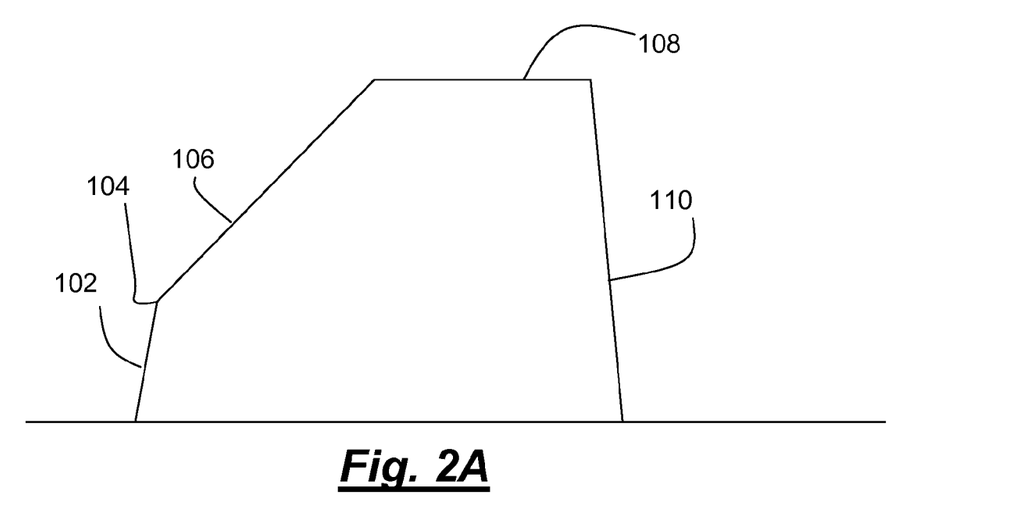
FIGS. 2A-2D are various waveform diagrams illustrating electrotherapy pulses having characteristics beneficial for discomfort mitigation according to aspects of the invention.

The pacing waveform can be varied according to other embodiments by applying waveshaping techniques. FIG. 2A illustrates a waveform for a single pulse produced by one such approach. In this example, the waveshaping technique being applied is a variable slew rate limiting. This pulse begins with an initially fast rise time 102 until a point 104 where the slew rate is slowed to a more gradual rising edge 106. The peak amplitude 108 is maintained for a predetermined duration (e.g., on the order or milliseconds), after which time the pulse is truncated with a relatively fast falling edge 110.

In general, the effectiveness of a pacing pulse is correlated to the total charge (i.e., in coulombs) delivered across the duration of the pulse width. In a traditional pacing pulse, a higher pulse amplitude and shorter pulse duration could be used to deliver an effective charge sufficient to capture enough cells in the heart to initiate a heartbeat most efficiently. This could cause discomfort in subcutaneous or external pacing arrangements.

The more gradual rising edge 106 contributes to reducing the pulse's higher-order harmonics (i.e., high-frequency spectral power density). This result is beneficial to reducing the degree of stimulation of nerve and skeletal muscles, which in turn reduces the discomfort felt by the patient, while delivering an effective quantity of charge over the duration of the pulse so as to achieve sufficient cardiac cell capture.

One drawback of using a slower rising edge is a loss of efficiency in the operation of the pulse generator. Whereas trans-cutaneous (i.e., external) pacing is generally performed by line-powered devices, or devices having large-capacity batteries or easily-replaceable batteries and therefore is less concerned with operational efficiency, implantable devices have limited size and battery capacity, and replacement of the device or battery requires performing a surgical procedure to reach the device. Thus, operational efficiency is a substantial concern for implantable devices. In limited slew rate embodiments, producing the slowly-rising edge 106 involves greater internal dissipation of energy in the IPG, and does relatively little in the patient while the rising amplitude remains below the capture threshold. Thus, in the present embodiment, an initially fast rising edge 102 is employed to advance the pulse amplitude to a level ideally below the activation threshold of pain receptors or non-targeted musculature of the patient. This pain or discomfort threshold can be determined individually for each patient after implantation of the device according to one embodiment. In another embodiment, as a more coarse rule-of-thumb, the point 104 where the slew rate is slowed is set between ¼ and ½ of the peak amplitude 108.

Figure 2B:
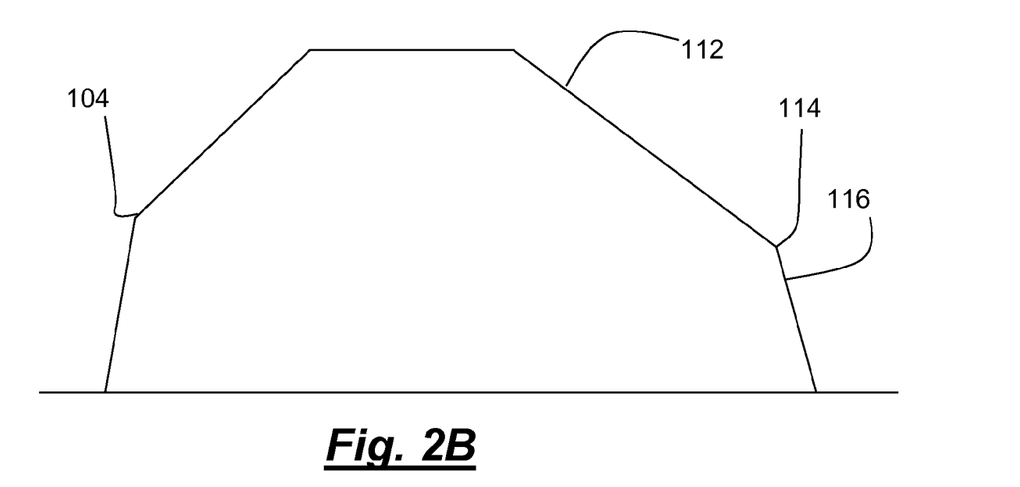

FIG. 2B illustrates a similar waveform according to another embodiment, in which the pulse is not truncated; rather, the peak is followed by a gradual falling edge 112 until point 114, after which a steep falling edge 116 concludes the pulse. In this approach, high-frequency components are further reduced with the more gradual transition on the trailing edges. Point 114 can be set to just below the threshold for stimulating pain receptors or activating non-targeted muscle cells, or it can be set to a nominal value relative to point 104 on the leading edge. As depicted, point 114 can be at a different level than leading edge transition point 104, taking into account any changes in the stimulation threshold as a result of the administration of the pulse.

Figure 2C:
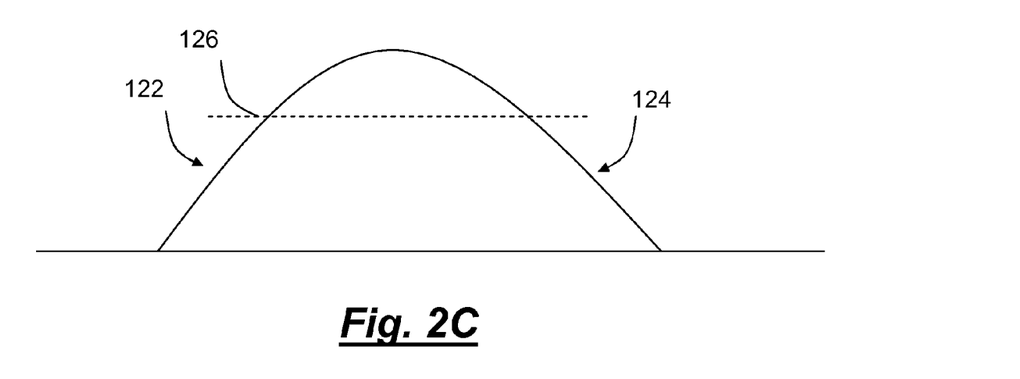

FIG. 2C illustrates a waveform according to another embodiment, in which the wave shape of the pulse is sinusoidal. As depicted, the pulse has the shape of a positive half-wave. Unlike the trapezoidal or modified-trapezoidal wave shape embodiments described above, this pulse has no flat, constant-amplitude portion. The rising and falling edges 122 and 124 respectively, are not distinctly defined in the overall wave shape, and they are not linear. This embodiment has the benefit of further reducing the spectral power distribution. A pure sine half-wave that begins and ends at zero amplitude has no discontinuities and minimal harmonics in its spectrum. The amplitude and fundamental frequency of the waveform is set such that the duration of the pulse which meets or exceeds the pacing threshold (i.e., having an amplitude greater than pacing threshold 126) is sufficiently long to ensure cardiac cell capture (e.g., 3-8 ms).

Figure 2D:
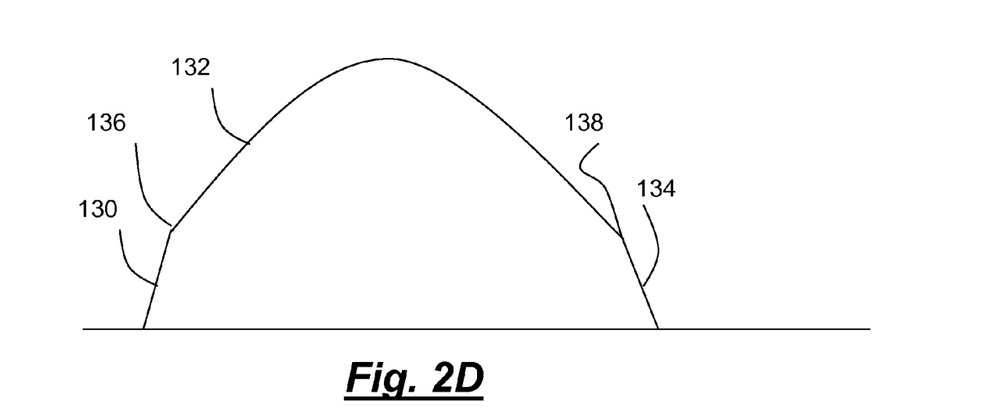

FIG. 2D illustrates a waveform according to a related embodiment that has a compound waveshape having an initially fast rise time 130, followed by a sinusoidal portion 132, which is in turn followed by a fast falling edge 134. The sinusoidal portion takes up a majority of the pulse duration. The transition points 136 and 138 are selected at amplitudes corresponding to the nerve or non-cardiac muscle stimulation thresholds. This waveform represents a trade-off between improved operating efficiency at the initial and final fast edges, and increased spectral content as a result of the non-differentiable current at the transition points 136 and 138.

Figure 3:
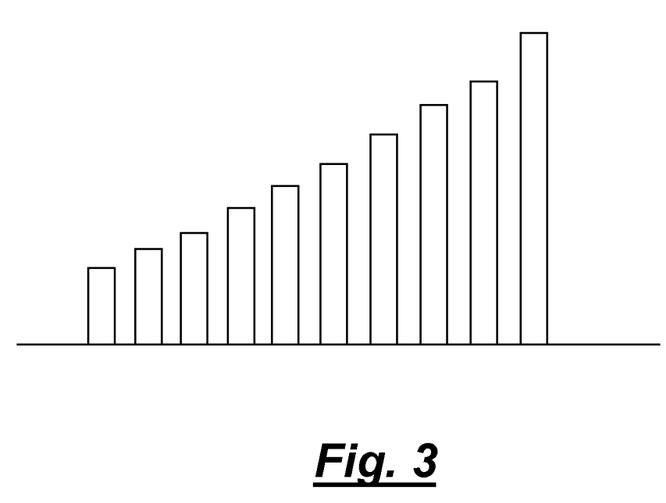
FIG. 3 is a waveform diagram illustrating a series of electrotherapy pulses with each successive pulse having a greater pulse amplitude than its preceding pulse according to one type of embodiment.

In a related embodiment, as depicted in FIG. 3, the pulse amplitude is ramped up across a series of pulses with each pulse having a peak amplitude higher than the preceding pulse. The step-wise pulse amplitude increases within a series of pulses can be halted when the device detects that cardiac cells have been successfully captured. Known techniques for detecting cardiac capture (e.g., impedance measurement across a region that includes the heart) can be employed to this end. The effective pulse amplitude for a treated arrhythmia episode can be stored on-board the IPG and used to calculate the initial amplitude at the beginning of the following arrhythmia episode. The pulses are shown in FIG. 3 as having basic square waveforms for the sake of simplicity. However, the principle of varying the amplitude of successive pulses is applicable to any waveform described herein, including the waveforms of FIGS. 2A-2D, as well as others not specifically described.

Figure 4:
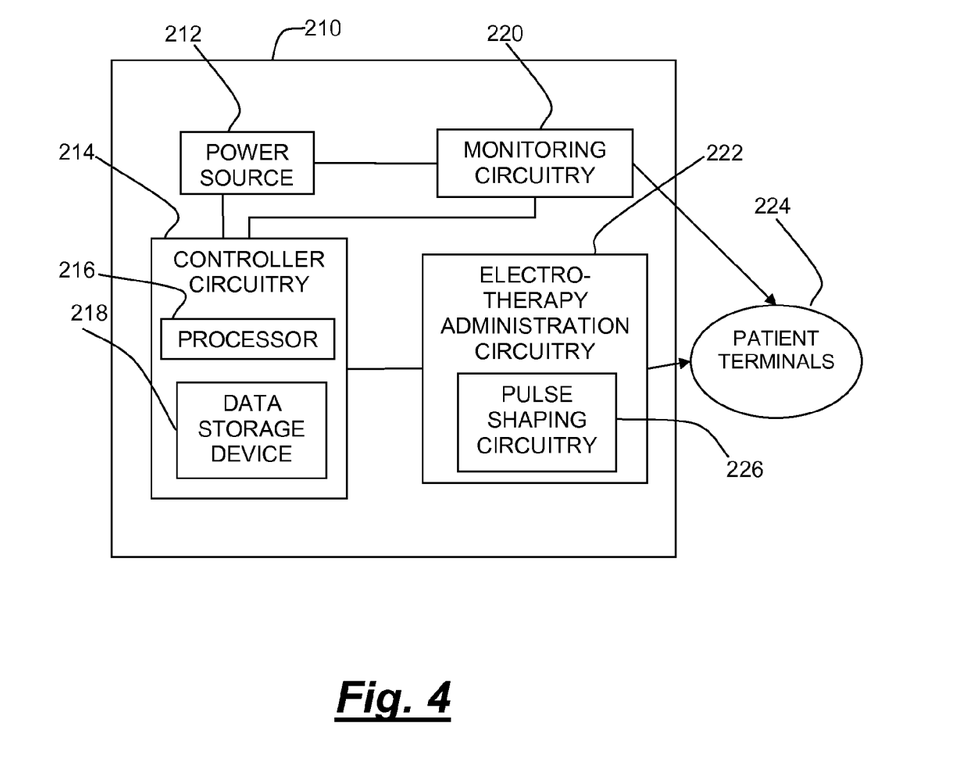
FIG. 4 is a block diagram illustrating a subcutaneous electrotherapy device according to aspects of the invention.

FIG. 4 is a block diagram illustrating an implantable pacing system 210 adapted for far-field pacing (without a trans-venous lead) according to one embodiment. The electrotherapy administration circuitry 222 is electrically coupled to the patient terminals 224, which can be selectively connected to subcutaneously-implanted electrodes or to the housing of the device (i.e., the can). The electrotherapy administration circuitry 222 generates and delivers pulses having specified parameters. Electrotherapy administration circuitry 222 includes pulse shaping circuitry 226, which is constructed to adjust the parameters of the pulses, including the waveform, pulse width, pulse period, pulse amplitude and pulse slew rate in response to a control signal. The monitoring circuitry 220 is electrically coupled to the patient terminals 224 as well as the power source 212 and is constructed to monitor the patient for indicia of arrhythmia. The monitoring circuitry 220 can further include sensing circuitry to detect physiologic responses to the electrotherapy. Examples of such sensing circuitry include electromyography (EMG) sensing circuitry coupled to the patient terminals, an accelerometer positioned in the housing of the device, a minute ventilation sensing arrangement, impedance measurement circuitry, hemodynamic sensors or other cardiac rhythm management sensors known in the art. The physiologic responses can be indicators of effectiveness of the electrotherapy (e.g., cardiac cell capture), possible discomfort exhibited by the patient, or a combination thereof.

Power source 212 contains an on-board energy store sufficient to power the device and to generate the electrotherapy energy. Any suitable battery technology known in the art may be employed. The controller circuitry 214 is electrically coupled to the power source 212, monitoring circuitry 220 and the electrotherapy administration circuitry 226. The controller circuitry includes a processor circuit 216, associated interface circuitry (not shown), which can include analog-todigital converting circuitry, digital-to-analog converting circuitry, address and data busses, communication circuitry to facilitate data input/output exchange with an external communicator, and a data storage device 218. The controller circuitry 214 stores program instructions that define all aspects of the operation of the device, including decision logic to administer electrotherapy, the electrotherapy waveforms and logic for selecting or adjusting the waveform parameters, logic for monitoring the patient and initiating, ceasing, or adjusting the electrotherapy in response, discomfort management control logic, and the like. These instructions are stored in data storage device 218, which is a non-transitory, machine-readable storage medium, such as a non-volatile memory device. Storage device 218 also stores the various electrotherapy parameters In operation, controller circuitry 214 can monitor the output from the monitoring circuitry 220 to determine when therapy is appropriate and to modify the parameters of the electrotherapy during an arrhythmia episode being treated. When preferred parameters such as waveform parameters, pulse delivery vector, etc., are established, these parameters can be stored in the data storage device 218 and accessed by the processor 216 to control the delivery of the electrotherapy via the electrotherapy administration circuitry 222.

The electrotherapy administration circuitry 222 can be adapted to produce artificial pacing pulses, each delivering sufficient charge through the patient terminals 224 to capture cardiac cells and initiate a cardiac cycle. The amount of charge necessary may vary based on the positioning of the patient terminals 224.

Figure 5:
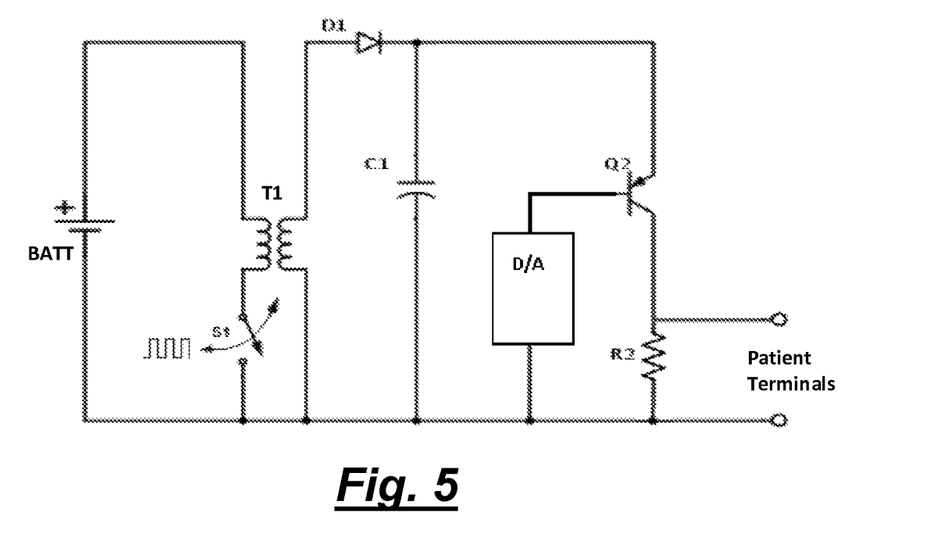
FIG. 5 is a diagram illustrating an example pulse shaping circuit according to one aspect of the invention.

FIG. 5 is a simplified circuit diagram of electrotherapy administration circuitry according to one example embodiment, which represents a circuit constructed to produce selected waveforms such as the ones described above with reference to FIGS. 2A-2D and FIG. 3. Switch S1 is cycled rapidly (and with variable duty cycle) to repetitively energize transformer T1, which is configured in a flyback converter arrangement to boost the voltage from the battery power source BATT. Transformer T has a primary-to-secondary winding ratio of n:m, with m being greater than n to increase the voltage on the secondary side. The winding ratio is also selected in accordance with the operating duty cycle, as per conventional flyback circuit design practices. The secondary side of T1 produces an output current through the rectifying diode D1, which charges capacitor C1. The voltage on capacitor C1 is thus maintained at the desired far-field pacing level of 10-60 volts, for example, and this voltage can be adjusted to some extent by the duty cycle control of switch S1, to which the control signal can be provided by the controller or an adjustable pulse-width modulation (PWM) circuit controlled by the controller. A digital-to-analog converter circuit D/A generates a signal corresponding to the desired waveshape and timing requirements for the waveform. The D/A circuit is interfaced with the controller, which ultimately selects and defines the waveform according to its program logic. The output of the D/A circuit is fed to output driver Q2 to deliver the pacing waveform to the patient terminals. In the simplified embodiment depicted, output driver is an inverting configuration, requiring the output of the D/A circuit to be inverted. Various other circuit topologies are contemplated according to related embodiments, with the possibility of using any suitable topology capable of providing the electrotherapy waveforms described herein, including, for instance, a push-pull amplifier output stage, a feedback controlled-amplifier circuit, etc.

One notable feature of this type of electrotherapy administration circuit is the use of an active load in the driver stage. This differs from certain conventional IPG circuits in that conventional circuits typically use fast switching to create square or steep trapezoidal waveshapes, or truncated exponential waveshapes produced by capacitive discharge. In this embodiment, the circuit drives the desired waveform like an electrical function generator. This advanced waveshaping technique facilitates variably-controlled rise and fall times of the leading and trailing edges of pulses, as well as compound waveforms with multiple, time-controlled, slew rates, and sinusoidal and other waveforms, which can be software-defined in the controller.

Figure 6:
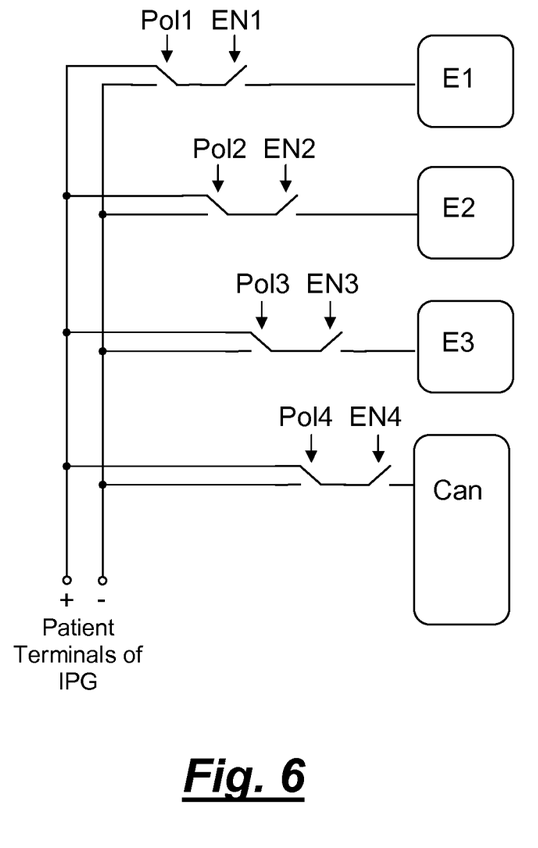
FIG. 6 is a diagram illustrating a switching arrangement for selecting an electrotherapy application vector according to one embodiment.

FIG. 6 illustrates an electrode selection arrangement for a subcutaneous device according to one embodiment. The patient terminals of the IPG are selectively connectable to each of a set of electrodes positioned at different locations in the patient. The metal housing of the IPG, i.e., the can, can itself serve as an electrode. In this exemplary switching arrangement, each electrode E1-E3 and the Can can be separately enabled or disabled according to a respective enable signal EN1-EN4. Also, each electrode can be selectively coupled to either the + or the − terminal of the patient terminals, facilitated by polarity selector switches POL1-POL4. This selection facilitates variation of the pulse polarity, as may be called for by the electrotherapy administration algorithm implemented in the controller. The various possible electrode and polarity combinations (including selecting individual or electrically-connected groups of electrodes to be the cathode and anode for a given electrotherapy application), are each an individual electrotherapy application vector. As will be described in greater detail below, one aspect of the invention is directed to adjusting the vector to mitigate patient discomfort.

In one embodiment, device 210 includes provisions for inferring discomfort in the patient evoked by application of the electrotherapy. According to one exemplary arrangement, monitoring circuitry 220 includes evoked response sensing circuitry that is constructed to sense indicia of discomfort response in the patient. One such indicator is movement in the patient. In an example embodiment, the evoked response sensing circuitry includes an accelerometer device. The controller circuitry 14 can be configured to infer evoked discomfort responses in the form of sudden motion sensed by the accelerometer that is temporally correlated with the application of electrotherapy. According to one algorithm for inferring evoked discomfort response, in a time window that begins immediately, or at a defined time delay measured from the start of each pulse, for example, if a sudden motion is detected and, optionally, if this motion appears over a defined number of pulses, a discomfort response is recognized by the controller.

In a related embodiment, EMG sensing using some or all of the subcutaneous electrodes available for electrotherapy application (e.g., electrodes not being used for the presently-applied vector, or even the same electrodes), or using separate electrodes from the electrotherapy-administering electrodes, is employed to sense signaling to the patient's musculature. In the EMG sensing, known techniques for filtering and other signal processing can be employed in the controller to obtain an EMG detection of suitable quality. In similar fashion to the time correlating determination exemplified above for movement sensing via accelerometer, the EMG sensing is detected in the monitoring window associated with each applied pulse, and an inference is made based on a period of observation over one or more pulses. This evoked discomfort response can be used to improve parameters for electrotherapy application.

The monitoring circuitry can also detect effectiveness of the electrotherapy. For instance, measurement of impedance across the heart can indicate whether a heartbeat was triggered by a pacing pulse. Various known sensing and detection techniques to measure effectiveness of electrotherapy can be utilized in different embodiments.

A related aspect of the invention involves inferring discomfort experienced by the patient during administration of electrotherapy and using that discomfort data to vary the parameters of administering the electrotherapy. The discomfort inference can be achieved via the evoked response sensing described above. The variation of parameters can include one or more of the following:

waveform amplitude adjustment;
basic waveshape selection (e.g., truncated, trapezoidal, sinusoidal, etc.);
compound waveform selection;
slew rate adjustment;
compound slew rate selection;
compound waveform/slew rate transition point adjustment;
electrotherapy administration vector selection (including polarity selection).

A wide variety of adjustment algorithms are contemplated according to various embodiments. In one high-level example, discomfort response criteria manages selection or adjustment of electrotherapy parameters in the following order or precedence (from highest to lowest):

(1) electrotherapy effectiveness (i.e., effective conversion of arrhythmia);
(2) discomfort mitigation
(3) operational efficiency.

Thus, in this example, of primary concern is treatment of the patient's arrhythmia. In a related embodiment, some level of discomfort (with defined limits) is acceptable based on a defined trade-off that can depend on the severity of the arrhythmia being experienced. For instance, a more severe tachycardia that, if untreated, can lead to a life-threatening condition, would call for more aggressive ATP treatment and a greater discomfort allowance. On the other hand, a less-severe arrhythmia would not require such aggressive treatment, and indeed, the order of precedence of (1) and (2) above may be reversed in those cases. There are numerous permutations of parameter variability contemplated. Notably, it is possible to have predefined a default ordering, and still further, in one embodiment, different orderings may be defined, with a particular ordering set being selected based on a historic result of parameter variation in the patient.

Figure 7:
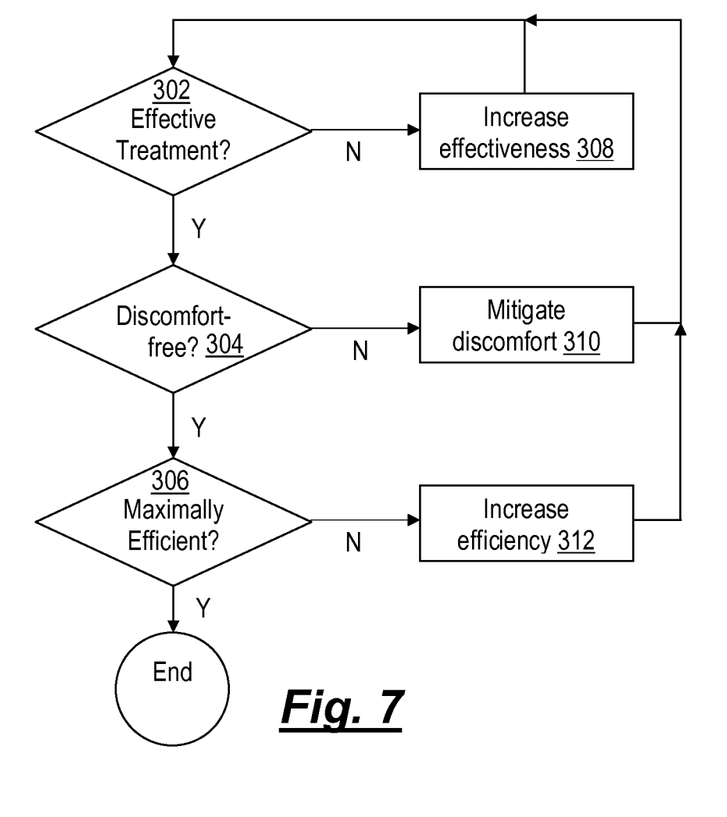
FIG. 7 is a flow diagram illustrating steps to automate optimization of electrotherapy administration such as far-field pacing by a subcutaneous device according to one embodiment.

FIG. 7 is a flow diagram illustrating an exemplary process of optimizing the electrotherapy parameters while taking discomfort into account, which uses the primary order of precedence of (1)-(3) outlined above. At 302, electrotherapy effectiveness monitoring is used to determine if the treatment is effective (i.e., are pacing pulses achieving capture of the heart to initiate a heartbeat?). If not, a subroutine to increase the effectiveness is called at 308. In one embodiment, this subroutine first adjusts the application vector, then the waveform, then the pulse amplitude. Other orders of operation are contemplated in various related embodiments. In a related embodiment, successful and unsuccessful combinations of electrotherapy parameters are stored for future reference. These stored values may have an expiration date associated with them to account for changes over time that can render such results obsolete.

If the electrotherapy is effective, the optimization routine advances to decision 304 in which the evoked discomfort response inference is checked to infer if the patient is experiencing discomfort. If the patient is not discomfort-free, then a discomfort mitigation subroutine is called at 310 to vary electrotherapy parameters. In one exemplary subroutine, parameters associated with unsuccessful electrotherapy effectiveness, and less aggressive variations of those parameters, are excluded from the set of possible parameters to try. In one specific approach, the electrotherapy parameters are varied in the following order to address discomfort: vector, pulse amplitude, waveform. Successful and failed parameter adjustments relating to discomfort are stored (temporarily or otherwise) for future reference. To ensure efficacy, effectiveness is checked by looping back to decision 302.

With items (1) and (2) being taken care of, i.e., effective electrotherapy being applied and discomfort being managed, the process proceeds to decision 306 to explore opportunity to adjust parameters to reduce energy consumption (i.e., battery drain) and therefore increase operational efficiency and life of the implanted device. Accordingly, if the electrotherapy is not maximally efficient (i.e., at the lowest pulse amplitude and using the sharpest waveform), then a subroutine to increase efficiency is called at 312. This subroutine can avoid failed configuration parameter combinations from subroutines 308 and 310. In one embodiment, the parameters are varied in the following order: pulse amplitude, waveform, vector.

In one example of varying some of the parameters in response to the evoked discomfort response, a set of therapy delivery vectors best adapted to reduce discomfort is selected along with the pulse amplitude. The controller circuitry is configured to deliver a first therapeutic stimulation at an initial amplitude to vector A and observe an evoked response (cardiac capture), then to deliver a second stimulation using vector B and observe the evoked response in a similar way. This procedure can be followed until all vectors have been evaluated. The performance of each vector can be compared and the vector with the best performance is utilized for sensing, discomfort control or therapy. If one vector results in the desired treatment outcome, that vector is utilized and the device then seeks to reduce any discomfort (e.g., reducing the pulse amplitude by a defined step size such as 10%, for example) and monitors the cardiac response in terms of capture for ATP. If the desired therapeutic result is not achieved the amplitude can be increased for the last successful vector with the lowest effective amplitude. In this way the optimum vector can be found that uses the lowest amplitude resulting in the lowest possible discomfort induced by the therapeutic stimulus.

When the therapeutic result is not achieved the amplitude is increased to the last effective amplitude that is then used for the remaining therapy. These vectors may be tested before discharging the patient from the hospital and the lower discomfort vectors stored in the data storage device of the controller. These vectors may also be tested and stored during an arrhythmia episode or during patient follow-up sessions.

In a related embodiment, instead of, or in addition to, automated adjustment of waveform and vector based on inferred discomfort response, the patient's feedback can be taken into account. In one approach, the data storage device is configured to store a list of pre-qualified pacing vectors, waveforms, and their appropriate minimum amplitudes that have been approved for therapy in the specific patient by a physician as part of in-clinic threshold testing. Notably, different thresholds can be defined for anti-bradycardia and anti-tachycardia pacing. Also, a set of amplitudes, vectors, and waveforms can be separately defined for different tachycardia heart rates to particularly manage the ventricular effective refractory period (VERP) phenomenon in which the pacing threshold increases with increased tachycardia rates. Rather than using a high setting and low setting as known in conventional devices, determining patient-specific parameter settings can allow for better discomfort mitigation using all of the available variables provided by aspects of the present invention.

If the patient reports discomfort, then the patient or other clinical staff (such as a nurse or primary care physician) can then use a programming interface to vary the parameter vector for therapy from among the pre-qualified set of approved electrotherapy parameters. When a new vector is selected, the device will begin using that vector and the minimum amplitude determined by the physician.

In a related embodiment, the patient-based feedback can be used together with automated inferred evoked response-based adjustment. In one such approach, the automated adjustment is configured to make finer adjustments, whereas the patient-driven response can be used to make more dramatic changes to amplitudes and waveform parameters.

Figure 8A:
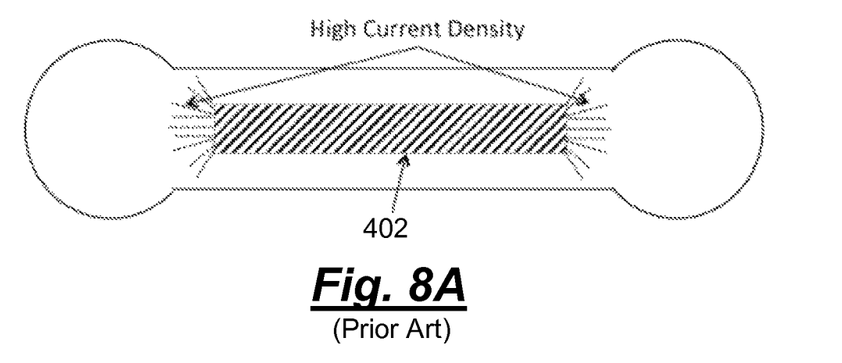
FIGS. 8A and 8B illustrate, respectively, a conventional subcutaneous electrode for use with an implantable pacemaker, and an improved lead having sensing electrodes that are utilized to reduce current density at the fringes of the primary electrode, according to one embodiment of the invention, which is beneficial for mitigating discomfort.
Figure 8B:
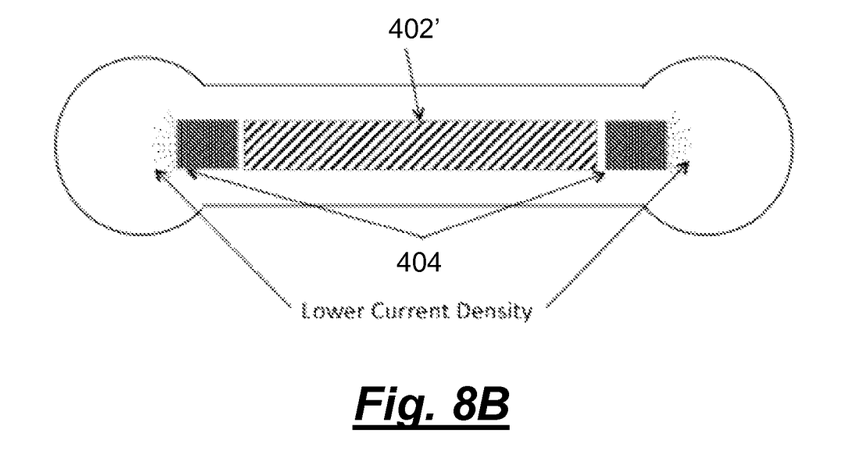

Another aspect of the invention relates to mitigating the discomfort experienced during therapy by reducing the edge effect of implanted leads in the body. FIG. 8A depicts an implantable lead for a subcutaneous system with a main stimulation coil 402. In this conventional system, the current density around the ends of the coil is very high during a stimulation pulse. This is because there is an abrupt fall-off in the potential at the ends. This "edge effect" causes increased nerve stimulation—and discomfort—since the higher current density captures more pain receptor neurons. In one embodiment of the invention, depicted in FIG. 8B, a reduced voltage is applied to two sensing electrodes 404 at each end of the coil in order to taper off the voltage and reduce the current density. Preferably, this reduced voltage would be 40-60% of the voltage on the main stimulation coil 402'.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

Any incorporation by reference of documents above is limited such that no subject matter is incorporated that is contrary to the explicit disclosure herein. Any incorporation by reference of documents above is further limited such that no claims that are included in the documents are incorporated by reference into the claims of the present Application. The claims of any of the documents are, however, incorporated as part of the disclosure herein, unless specifically excluded. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An electrotherapy apparatus for treating a patient experiencing an arrhythmia, the apparatus comprising:
   a power source adapted to supply energy for operation of the apparatus;
   electrotherapy administration circuitry electrically coupled to the power source and to a set of patient terminals, and constructed to generate electrotherapy pulses using the energy from the power source and apply a series of the electrotherapy pulses via the patient terminals in response to a control signal;
   monitoring circuitry electrically coupled with the power source and the set of patient terminals, and constructed to monitor the patient for indicia of the arrhythmia;
   controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses; and
   evoked response sensing circuitry electrically coupled to the controller circuitry, the evoked response sensing circuitry being constructed to sense indicia of movement by the patient, and the controller circuitry being further configured to infer whether the movement is an evoked response to the administration of the electrotherapy pulses, and to adjust application of subsequent electrotherapy pulses in response to an inference of the evoked discomfort response.

2. The electrotherapy apparatus of claim 1, wherein the evoked response sensing circuitry includes an accelerometer, and wherein the controller circuitry is configured to detect the evoked discomfort response based on sudden motion sensed by the accelerometer temporally correlated with application of the electrotherapy.

3. The electrotherapy apparatus of claim 1, wherein the set of patient terminals are selectively switchably couplable to a plurality different electrodes in response to an electrode selection signal generated by the controller circuitry, wherein each selected subset of the electrodes represents a corresponding electrotherapy application vector; and
   wherein the controller circuitry is configured to vary the electrotherapy application vector in response to the detection of the evoked discomfort response.

4. The electrotherapy apparatus of claim 1, wherein the controller circuitry is configured to vary a waveform parameter of the electrotherapy pulses in response to the detection of the evoked discomfort response.

5. The electrotherapy apparatus of claim 1, wherein the electrotherapy pulses are artificial pacing pulses, each delivering sufficient charge through a set of electrodes to initiate a cardiac cycle.

6. The electrotherapy apparatus of claim 1, wherein the electrotherapy pulses are far-field pacing pulses, each delivering sufficient charge, through a set of electrodes positioned in far-field fashion relative to a heart of the patient, to initiate a cardiac cycle.

7. The electrotherapy apparatus of claim 1, wherein the electrotherapy pulses are pacing pulses that have waveform, amplitude, and timing characteristics sufficient for treating a tachycardia arrhythmia.

8. The electrotherapy apparatus of claim 1, wherein the electrotherapy pulses each have an amplitude of between 30 and 80 mA and a pulse duration between 3 and 15 milliseconds.

9. The electrotherapy apparatus of claim 1, wherein the series of electrotherapy pulses includes a first pulse followed by a plurality of subsequent pulses, with each successive pulse having a greater pulse amplitude than its preceding pulse.

10. The electrotherapy apparatus of claim 1, wherein the set of patient terminals are electrically coupled to a set of electrodes implanted subcutaneously in the patient.

11. The electrotherapy apparatus of claim 1, wherein the electrotherapy administration circuitry includes a pulse shaping circuit comprising an adjustable slew rate limiter, wherein the pulse shaping circuit is constructed such that, in operation, the pulse shaping circuit applies a slew rate limit for at least a portion of each rising edge of each pulse of the series of electrotherapy pulses.

12. The electrotherapy apparatus of claim 11, wherein the adjustable slew rate limiter includes an active load through which the electrotherapy pulses are applied.

13. The electrotherapy apparatus of claim 11, wherein the pulse shaping circuit is constructed such that, in operation, the pulse shaping circuit applies the slew rate limit such that each rising edge of each pulse of the series of electrotherapy pulses has a relatively faster slew rate for an initial portion of the rising edge and a relatively slower slew rate for a latter portion of each rising edge.

14. The electrotherapy apparatus of claim 11, wherein said at least the portion of each rising edge of each pulse that is subject to the slew rate limit causes the corresponding pulse to evoke a reduced discomfort response in the patient relative to a pulse without that slew rate limit.

15. A method for treating a patient experiencing an arrhythmia, the method comprising:
- by an electrotherapy device, monitoring the patient for indicia of the arrhythmia;
- in response to a determination of a presence of the arrhythmia, generating and administering a series of electrotherapy pulses to the patient, by the electrotherapy device; and
- by the electrotherapy device, sensing indicia of movement by the patient;
- by the electrotherapy device, inferring whether the movement is an evoked discomfort response to the administration of the electrotherapy pulses; and
- by the electrotherapy device, adjusting application of subsequent electrotherapy pulses in response to an inference of the evoked discomfort response.

16. The method of claim 15, wherein sensing the indicia of movement by the patient includes reading an accelerometer, and wherein detection of the evoked discomfort response is based on sudden motion sensed by the accelerometer temporally correlated with application of the electrotherapy.

17. The method of claim 15, wherein adjusting the application of the subsequent electrotherapy pulses includes varying an electrotherapy application vector in response to the evoked discomfort response.

18. The method of claim 15, wherein adjusting the application of the subsequent electrotherapy pulses includes varying a waveform parameter of the electrotherapy pulses in response to the evoked discomfort response.

19. The method of claim 15, wherein the electrotherapy pulses are artificial pacing pulses, each delivering sufficient charge to the patient to initiate a cardiac cycle.

20. The method of claim 15, wherein the electrotherapy pulses are far-field pacing pulses, each delivering sufficient charge, in far-field fashion relative to a heart of the patient, to initiate a cardiac cycle.

21. The method of claim 15, wherein the electrotherapy pulses are pacing pulses that have waveform, amplitude, and timing characteristics sufficient for treating a tachycardia arrhythmia.

22. The method of claim 15, wherein the electrotherapy pulses each have an amplitude of between 30 and 80 mA and a pulse duration between 3 and 15 milliseconds.

23. The method of claim 15, wherein the series of electrotherapy pulses includes a first pulse followed by a plurality of subsequent pulses, with each successive pulse having a greater pulse amplitude than its preceding pulse.

24. The method of claim 15, wherein administering the series of electrotherapy pulses includes applying a slew rate limit for at least a portion of each rising edge of each pulse of the series of electrotherapy pulses.

25. The method of claim 24, wherein applying the slew rate limit includes causing each rising edge of each pulse of the series of electrotherapy pulses to have a relatively faster slew rate for an initial portion of the rising edge and a relatively slower slew rate for a latter portion of each rising edge.

26. The method of claim 24, wherein said at least the portion of each rising edge of each pulse that is subject to the slew rate limit causes the corresponding pulse to evoke a reduced discomfort response in the patient relative to a pulse without that slew rate limit.

\* \* \* \* \*